United States Patent
Okamoto et al.

(10) Patent No.: US 11,479,738 B2
(45) Date of Patent: Oct. 25, 2022

(54) FRAGRANCE COMPOSITION CONTAINING ALPHA-METHOXYISOBUTYRIC ESTER COMPOUND, AND USE THEREOF AS FRAGRANCE

(71) Applicant: MITSUBISHI GAS CHEMICAL COMPANY, INC., Chiyoda-ku (JP)

(72) Inventors: Atsushi Okamoto, Niigata (JP); Umi Yokobori, Niigata (JP); Eriko Kushida, Niigata (JP); Masaki Takemoto, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 24 days.

(21) Appl. No.: 17/255,224

(22) PCT Filed: Jun. 26, 2019

(86) PCT No.: PCT/JP2019/025397
§ 371 (c)(1),
(2) Date: Dec. 22, 2020

(87) PCT Pub. No.: WO2020/004469
PCT Pub. Date: Jan. 2, 2020

(65) Prior Publication Data
US 2021/0269744 A1    Sep. 2, 2021

(30) Foreign Application Priority Data

Jun. 26, 2018 (JP) .............................. JP2018-121114
Nov. 28, 2018 (JP) .............................. JP2018-222721

(51) Int. Cl.
*C11B 9/00* (2006.01)
*C07C 69/708* (2006.01)

(52) U.S. Cl.
CPC .......... *C11B 9/0019* (2013.01); *C07C 69/708* (2013.01); *C11B 9/003* (2013.01); *C07C 2601/08* (2017.05); *C07C 2601/14* (2017.05)

(58) Field of Classification Search
CPC ....... C11B 9/0019; C11B 9/003; C07C 69/67; C07C 69/708; C07C 2601/08; C07C 2601/14
See application file for complete search history.

(56) References Cited

U.S. PATENT DOCUMENTS

| 2,525,249 A | 10/1950 | Weizmann |
| 3,368,943 A | 2/1968 | Gilbert et al. |
| 6,509,312 B1 | 1/2003 | Giersch |

FOREIGN PATENT DOCUMENTS

| EP | 1016699 A1 * | 7/2000 | ............... C09D 9/00 |
| JP | 54-92635 A | 7/1979 | |
| JP | 7-228895 A | 8/1995 | |
| JP | 8-67884 A | 3/1996 | |
| JP | 8-231 990 A | 9/1996 | |
| JP | 2015-18667 A | 1/2015 | |
| JP | 2015018667 A * | 2/2015 | ............. Y02E 60/10 |

OTHER PUBLICATIONS

JP 2015018667, Kodama, K. et al., Electrolyte for nonaqueous secondary battery, nonaqueous secondary battery and additive for nonaqueous electrolyte, English translation, 50 pages (Year: 2015).*
International Search Report dated Aug. 27, 2019 in PCT/JP2019/025397 filed on Jun. 26, 2019, 1 page.
"Gousei Koryo: Kagaku to Shohin Chishiki, zoho shinban (Synthetic fragrance: chemistry and product knowledge, new enlarged edition)," The Chemical Daily Co. Ltd., 2016, pp. 580 to 583, 4 total pages.

* cited by examiner

*Primary Examiner* — Yate' K Cutliff
(74) *Attorney, Agent, or Firm* — Oblon, McClelland, Maier & Neustadt, L.L.P.

(57) ABSTRACT

A fragrance composition comprising a compound represented by Formula (1): wherein, in Formula (1), R represents a linear or branched alkyl group having from 2 to 3 carbon atoms or a cyclic alkyl group having from 3 to 6 carbon atoms.

4 Claims, No Drawings

FRAGRANCE COMPOSITION CONTAINING ALPHA-METHOXYISOBUTYRIC ESTER COMPOUND, AND USE THEREOF AS FRAGRANCE

TECHNICAL FIELD

The present invention relates to fragrance compositions containing α-methoxyisobutyric ester compounds, and use thereof as fragrances.

BACKGROUND ART

Some isobutyric esters are known to be compounds useful as fragrances. For example, Non Patent Document 1 describes that various isobutyric esters are mainly used as flavors, and all these isobutyric esters are flavor materials having a fruit scent; specifically, methyl isobutyrate gives a sweet apricot-like scent, propyl isobutyrate gives a strong pineapple-like scent, butyl isobutyrate gives a fresh apple- and banana-like scent, and isoamyl isobutyrate gives a sweet apricot- and pineapple-like scent.

Additionally, Patent Document 1 discloses that linear or branched saturated alkyl esters having from 4 to 12 carbon atoms of α-alkoxyisobutyric acid are useful as fragrances, describing n-hexyl α-ethoxyisobutyrate having a lavender-like aroma, and each of the isobutyl ester, n-pentyl ester, and n-hexyl ester of α-methoxyisobutyric acid having fragrance characteristics and being suitable for use in detergents including chlorine-based bleach.

On the other hand, ethyl α-methoxyisobutyrate is a known substance. For example, Patent Documents 2 to 3 and the like disclose that ethyl α-methoxyisobutyrate is useful as a low-toxic and highly safe solvent for wax cleaning agents, flux cleaning agents, resist stripping agents, and the like. Although it is disclosed that the odor of ethyl α-methoxyisobutyrate includes "no unpleasant odor", there is no description about the fragrance characteristics thereof, fragrance compositions containing the same, and methods for use as a fragrance.

CITATION LIST

Patent Documents

Patent Document 1: U.S. Pat. No. 3,368,943
Patent Document 2: JP H08-231990 A
Patent Document 3: JP H07-228895 A

Non Patent Document

Non-Patent Document 1: "Gousei Koryo: Kagaku to Shohin Chishiki, zoho shinban (Synthetic fragrance: chemistry and product knowledge, new enlarged edition)", The Chemical Daily Co. Ltd., 2016, pp. 580 to 582

DISCLOSURE OF THE INVENTION

Technical Problem

An object to be solved by the present invention is to provide a fragrance composition containing an α-methoxyisobutyric ester compound, which is useful as a fragrance and as a fragrance ingredient, as an active ingredient, and use of the compound as a fragrance.

Solution to Problem

The present inventors have synthesized various compounds and have made diligent research of the aromas thereof. Thus, the present inventors discovered that particular ester compounds of α-methoxyisobutyric acid are useful as fragrances and fragrance ingredients.

That is, the present invention is as follows.

<1> A fragrance composition comprising a compound represented by Formula (1) as an active ingredient:

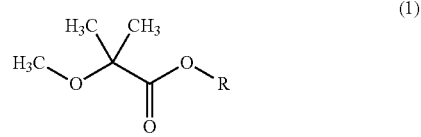

wherein, in Formula (1), R represents a linear or branched alkyl group having from 2 to 3 carbon atoms or a cyclic alkyl group having from 3 to 6 carbon atoms.

<2> The fragrance composition according to <1>, wherein, in Formula (1), R is selected from the group consisting of a n-propyl group, an isopropyl group, and a cyclopentyl group.

<3> Use of a compound represented by Formula (1) as a fragrance:

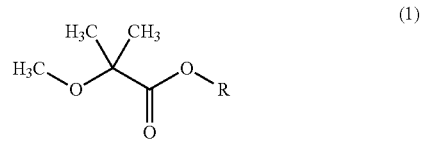

wherein, in Formula (1), R represents a linear or branched alkyl group having from 2 to 3 carbon atoms or a cyclic alkyl group having from 3 to 6 carbon atoms.

<4> The use according to <3>, wherein, in Formula (1), R is selected from the group consisting of a n-propyl group, an isopropyl group, and a cyclopentyl group.

<5> The use according to <3> or <4>, wherein the compound represented by Formula (1) imparts a mint-like scent.

<6> The use according to <3> or <4>, wherein the compound in which R is an isopropyl group in Formula (1) imparts a damascone-like fruity-tone, floral-tone, or woody-tone scent.

Advantageous Effects of Invention

According to the present invention, it is possible to provide a fragrance composition containing an α-methoxyisobutyric ester compound, which is useful as a fragrance and as a fragrance ingredient, as an active ingredient, and use of the compound as a fragrance.

DESCRIPTION OF EMBODIMENTS

[Fragrance Composition and Use]

A fragrance composition of the present invention comprises a compound represented by Formula (1) below as an active ingredient. Furthermore, use of the present invention is use of the compound represented by Formula (1) below as a fragrance.

The present invention will be described in detail hereinbelow.

<Compound Represented by Formula (1)>

The compound to be used in the fragrance composition of the present invention and the use of the present invention is represented by Formula (1) below: (hereinbelow, also referred to as the "isobutyric ester according to an embodiment of the present invention")

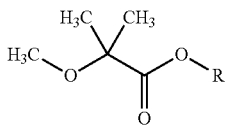

(1)

wherein, in Formula (1), R represents a linear or branched alkyl group having from 2 to 3 carbon atoms or a cyclic alkyl group having from 3 to 6 carbon atoms.

In Formula (1), R is specifically an ethyl group, a n-propyl group, an isopropyl group, a cyclopropyl group, a cyclobutyl group, a cyclopentyl group, a cyclohexyl group, or the like.

The compound represented by Formula (1), which is useful as a fragrance and a fragrance ingredient, has a mint-like aroma as well as simultaneously exhibits an aroma of a citrus tone, floral tone, spicy tone, or the like.

The compound is preferably a compound in which R is selected from the group consisting of a n-propyl group, an isopropyl group, and a cyclopentyl group.

Particularly preferably, R is a n-propyl group.
Particularly preferably, R is an isopropyl group.
Particularly preferably, R is a cyclopentyl group.

In an embodiment of the present invention, examples of the compound represented by Formula (1) include compounds represented by any of Formulas (1-1) to (1-7) below, and the particularly preferred compounds include compounds represented by any of Formulas (1-1) to (1-3) below.

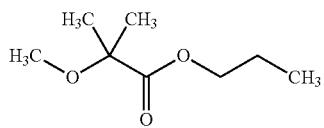

(1-1)

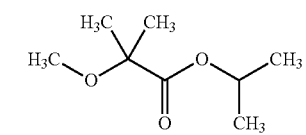

(1-2)

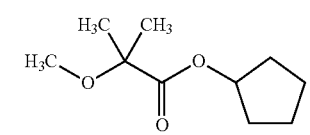

(1-3)

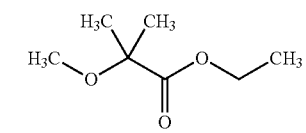

(1-4)

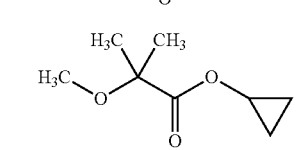

(1-5)

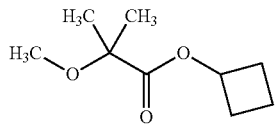

(1-6)

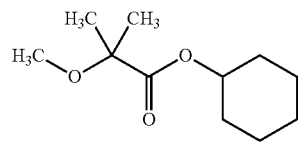

(1-7)

In recent years, there is a trend to focus more on the toxicity and environmental impact of chemicals, and fragrances or fragrance compositions are no exception. There is an increase in the number of cases where a fragrance which has been used in the past is severely restricted in usage conditions or is prohibited from use due to their sensitization properties to a human body, tendency to accumulate in the environment, and the like. Thus, there is a strong demand for a fragrance and a fragrance composition having a lower environmental impact. Accordingly, fragrance ingredients also preferably have excellent biodegradability and show a low degree of bioaccumulation.

The compound represented by Formula (1) contains a compound excellent in biodegradability and showing a low degree of bioaccumulation, and from this perspective, R is preferably a group selected from the group consisting of a n-propyl group, an isopropyl group, and a cyclopentyl group.

The compound represented by Formula (1) is useful as a fragrance because the compound has an excellent aroma as described below. Generally, a fragrance is rarely used alone, and often used in a fragrance compound (fragrance composition) produced by compounding a plurality of fragrances in accordance with the purpose. The compound represented by Formula (1) is useful as a fragrance (also called a "fragrance ingredient") to be blended in a fragrance compound (fragrance composition), and the fragrance composition of the present invention contains the compound represented by Formula (1) as an active ingredient. As the fragrance, one of the compounds represented by Formula (1) above may be used alone or two or more of the compounds may be used in combination.

Additionally, the compound represented by Formula (1) may include a small amount of impurities, by-products, contaminants, and the like as long as the effects of the present invention are not compromised.

The compound represented by Formula (1) has a mint-like aroma as well as an aroma of citrus-tone, floral-tone, spicy-tone, or the like, and also is excellent in diffusivity. Further, the compound represented by Formula (1-2) has a damascone-like fruity-tone, floral-tone, or woody-tone aroma, and also is excellent in diffusivity.

The compound represented by Formula (1) may be used alone as a fragrance and added to various perfumery and cosmetics, healthcare and sanitary materials as well as medicinal supplies, household goods, foods, and the like to thereby impart an aroma thereto. Alternatively, the compound represented by Formula (1) may be mixed with another fragrance ingredient or the like to prepare a fragrance composition (fragrance compound) described below, which may be blended into a variety of products to impart an aroma. Among these, from the perspective of obtaining an intended aroma, it is preferred that the compound represented by Formula (1) be blended in a fragrance composition as a fragrance ingredient to prepare a fragrance composition containing the compound represented by Formula (1) as an active ingredient and the fragrance composition be blended in a product to perfume the product.

Additionally, the compound represented by Formula (1) is preferably used as a fragrance and is more preferably used to impart a mint-like scent. Furthermore, the compound represented by Formula (1-2) is more preferably used to impart a damascone-like fruity-tone, floral-tone, or woody-tone scent.

<Fragrance Composition>

The fragrance composition (fragrance compound) of the present invention contains the compound represented by Formula (1) as an active ingredient. Note that the fragrance composition is not particularly limited as long as it contains at least one compound represented by Formula (1), and two or more compounds represented by Formula (1) may be included.

The fragrance composition according to an embodiment of the present invention is only required to contain the compound represented by Formula (1) as an active ingredient, and other ingredients are not particularly limited. However, the fragrance composition preferably contains another fragrance ingredient (hereinafter, also referred to as a "known fragrance").

Note that the "fragrance composition (fragrance compound)" is a composition that is added to various perfumery and cosmetics, medicinal supplies, foods, beverages, and the like to impart an aroma thereto, or a composition that is used as it is in a perfume or the like. The fragrance composition may contain an additive such as a solvent, as required, in addition to the known fragrance.

The amount of the compound represented by Formula (1) blended depends on the type of the compound, the type of aroma intended, the intensity of the aroma, and the like. The amount of the compound represented by Formula (1) in the fragrance composition is preferably 0.001 mass % or greater, more preferably 0.01 mass % or greater, and even more preferably 0.1 mass % or greater, and preferably 90 mass % or less, more preferably 70 mass % or less, and even more preferably 50 mass % or less.

The known fragrance is not particularly limited as long as it is a known fragrance component, and a wide range of fragrances can be used. For example, one or two or more of the following fragrances can be selected and used at any mixing ratio.

Examples thereof include hydrocarbons such as limonene, α-pinene, β-pinene, terpinene, cedrene, longifolene, and valencene; alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-t-butylcyclohexanol, 4-methyl-2-(2-methylpropyl)tetrahydro-2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol, phenols such as eugenol, thymol, and vanillin; esters such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobronyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and FRUITATE; aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxy-3 (2H)-furanone, maltol, 7-acetyl-1,2,3,4,5,6,7,8-octahydro-1, 1,6,7-tetramethyl naphthalene, muscone, civetone, cyclopentadecanone, and cyclohexedecanone; acetals and ketals such as acetoaldehyde ethylphenylpropyl acetal, citraldiethyl acetal, phenylacetoaldehyde glycerin acetal, and ethyl acetoacetate ethyleneglycol ketals; ethers such as anethole, β-naphthylmethyl ether, β-naphthyl ethyl ether, limonene oxide, rose oxide, 1,8-cineol, and racemic or photoactive dodecahydro-3a,6,6,9a-tetramethylnaphtho[2, 1-b]furane; nitriles such as citronellyl nitrile; lactones such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, sandalwood, vetiver, patchouli, and labdanum; and other fragrance materials such as synthetic fragrances.

In addition, the fragrance composition may also contain, as components besides the fragrance ingredients, a surfactant such as polyoxyethylene lauryl sulfate ether; a solvent such as dipropylene glycol, diethyl phthalate, ethylene glycol, propylene glycol, methyl myristate, triethyl citrate, or the like; an antioxidant; a coloring agent; and the like.

The compound represented by Formula (1), which has a mint-like aroma and simultaneously has an aroma of a citrus tone, a floral tone, a spicy tone, or the like, can impart a natural citrus tone, a floral tone, or a spicy tone in addition to the mint tone when combined with a known fragrance. Thus, the compound is usefully added to various perfumery and cosmetics, healthcare and sanitary materials as well as to medicinal supplies, household goods, foods, and the like to thereby impart an aroma thereto. The isobutyric ester according to an embodiment of the present invention represented by Formula (1-2) is usefully combined with a known fragrance or the like to thereby impart an aroma because of having a damascone-like fruity-tone, floral-tone, or woody-tone aroma.

Examples of products to which a fragrance composition containing the compound represented by Formula (1) can be added to impart an aroma and improve the aroma of the blend object include various products such as perfumery and cosmetics, health and sanitary materials, miscellaneous goods, beverages, foods, quasi-pharmaceutical products, and medicinal supplies; the fragrance composition can be used as an aroma component in, for example, fragrance products such as perfumes and colognes; hair cosmetics such as shampoos, rinses, hair tonics, hair creams, mousses, gels, pomades, sprays, and the like; skin cosmetics such as skin lotions, essences, creams, milky lotions, packs, foundations, face powders, lipsticks, and various make-up products; various health and sanitary detergents such as dish washing detergents, laundry detergents, softeners, disinfecting detergents, anti-odor detergents, indoor fragrances, furniture cares, glass cleaners, furniture cleaners, floor cleaners, disinfectants, insecticides, bleaching agents, bactericides, repellants, and the like; quasi-pharmaceutical products such as toothpastes, mouthwashes, bath additives, antiperspirant products, and perming liquids; miscellaneous goods such as toilet paper and tissue paper; medicinal supplies; foods, and the like.

The amount of the fragrance composition blended in the product is not particularly limited, and the amount of the fragrance composition blended can be selected over a wide range, depending on the type, nature, and sensory benefits of the product to be perfumed. For example, the amount may be 0.00001 mass % or greater, preferably 0.0001 mass % or greater, and more preferably 0.001 mass % or greater. In the case of a fragrance such as perfume or the like, for example, the amount may be 100 mass %, preferably 80 mass % or less, more preferably 60 mass % or less, and even more preferably 40 mass % or less.

[Method for Producing Compound Represented by Formula (1)]

The production method of the compound represented by Formula (1) is not particularly limited and may be appropriately selected from known methods and used.

For example, an α-methoxyisobutyric ester can be produced by esterifying α-methoxyisobutyric acid with an alcohol in the presence of a catalyst. The reaction formula for this reaction is shown as Formula (2) below.

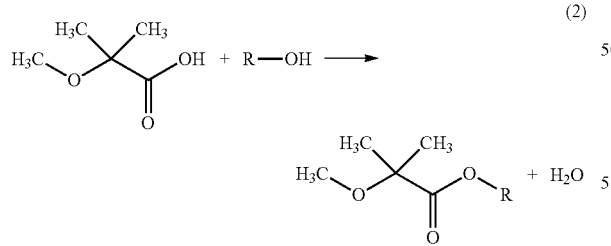

In Formula (2), R represents a linear or branched alkyl group having from 2 to 3 carbon atoms or a cyclic alkyl group having from 3 to 6 carbon atoms.

Further, a target α-methoxyisobutyric ester can be produced by transesterifying an α-methoxyisobutyric ester with an alcohol of different kinds in the presence of a catalyst. The reaction formula for this reaction is shown as Formula (3) below.

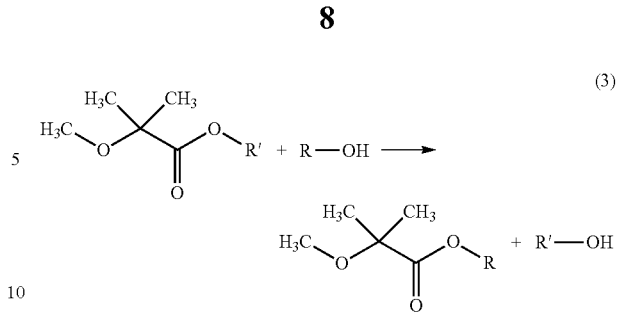

In Formula (3), R represents a linear or branched alkyl group having from 2 to 3 carbon atoms or a cyclic alkyl group having from 3 to 6 carbon atoms. R' is not particularly limited as long as it is an alkyl group different from R.

In addition, a target α-methoxyisobutyric ester can be produced by reacting an α-halogenoisobutyric ester with an alkali metal methoxide. The reaction formula for this reaction is shown as Formula (4) below.

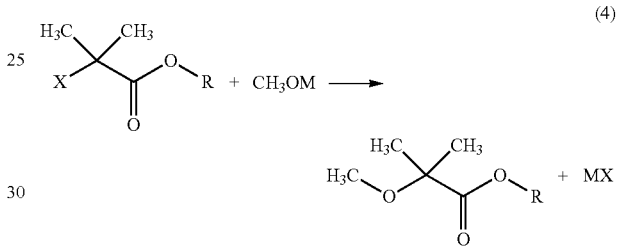

In Formula (4), R represents a linear or branched alkyl group having from 2 to 3 carbon atoms or a cyclic alkyl group having from 3 to 6 carbon atoms. M represents an alkali metal element such as sodium, potassium, cesium, or the like, and X represents a halogen element such as chlorine, bromine, iodine, or the like.

Further, a target α-methoxyisobutyric ester can be produced by reacting an α-hydroxyisobutyric ester or an alkali metal alkoxide of an α-hydroxyisobutyric ester with methyl halide. The reaction formula for this reaction is shown as Formula (5) below. The alkali metal alcoholate of the α-hydroxyisobutyric ester may be the one synthesized separately or may be the one produced by a reaction of an α-methoxyisobutyrate ester with an alkali metal hydride or the like in the reaction system.

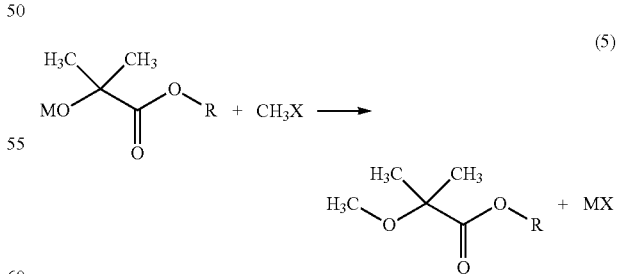

In Formula (5), R represents a linear or branched alkyl group having 2 to 3 carbon atoms or a cyclic alkyl group having 3 to 6 carbon atoms. M represents hydrogen or an alkali metal element such as sodium, potassium, cesium, or the like, and X represents a halogen element such as chlorine, bromine, iodine, or the like.

Known catalysts, reaction methods, reaction conditions, and reaction apparatus can be used as the catalyst, reaction method, reaction conditions, reaction apparatus, and the like to be used for these reactions, and there is no particular limitation thereon. In addition, as a method for purifying the obtained compound of Formula (1), a known purification method can be used, and there is no limitation thereon.

EXAMPLES

Hereinafter, the present invention will be described in further detail with reference to examples, but the present invention is not limited to these examples.
<Gas Chromatography (GC) Analysis Conditions>
Apparatus: GC-2010 (available from Shimadzu Corporation, trade name)
Detector: FID
Column: DB-1 (capillary column available from J&W Scientific, Inc., trade name) (0.25 mmφ×60 m×0.25 μm)

Reference Example 1: Synthesis of α-Methoxyisobutyric Acid 697.3 g of acetone (available from Wako Pure Chemical Industries, Ltd.) and 476.8 g of chloroform (available from Wako Pure Chemical Industries, Ltd.) were fed in a 2000-mL round-bottom flask equipped with a stirrer and a reflux condenser, and cooled to −7° C. 20.2 g of potassium hydroxide (available from Wako Pure Chemical Industries, Ltd.) was placed thereto. After a reaction under stirring for 2 hours, the temperature was slowly raised to 20° C., and stirring was further conducted for 30 minutes to complete the reaction. After the resulting reaction product was filtered and concentrated, ion exchanged water was added thereto to obtain a white precipitate. The white precipitate was filtered, washed and dried in vacuo (60° C., 30 hPa., 12 hours) to obtain 238.9 g of 1,1,1-trichloro-tert-butanol (chloretone) (purity by GC analysis (hereinafter, also referred to as GC purity): 95%).

Next, 95.0 g of ion exchanged water and 330.1 g of methanol (available from Wako Pure Chemical Industries, Ltd.) were placed in a 2000-mL 4-neck round-bottom flask equipped with a stirrer, a reflux condenser, and a dropping funnel, and 164.6 g of potassium hydroxide (available from Wako Pure Chemical Industries, Ltd.) was dissolved therein under cooling with ice. When the temperature of the flask was raised to 16° C., a solution of 130.6 g of 1,1,1-trichloro-tert-butanol produced by the above method dissolved in 327.2 g of methanol (available from Wako Pure Chemical Industries, Ltd.) was added dropwise from the dropping funnel. While the liquid temperature was maintained so as not to exceed 30° C. or more by controlling the drop rate and the cooling bath, the entire raw material solution was dropped over approximately 30 minutes. After completion of the dropping, the flask was refluxed for 2 hours under heating by an oil bath to perform the reaction. After completion of the reaction, the mixture was cooled to room temperature, and 500 mL of a 10% aqueous sulfuric acid solution was added and stirred. After a white precipitate produced was filtered and separated, the filtrate was extracted with diethyl ether four times, washed three times with a saturated aqueous solution of sodium chloride, dried over anhydrous sodium sulfate, and then concentrated to provide 42.3 g of an oily crude product. This product was distilled under reduced pressure to provide 24.8 g of α-methoxyisobutyric acid (GC purity: 99.8%) as a fraction at 46 hPa and 115° C.

Example 1: Synthesis of n-Propyl α-Methoxyisobutyrate

A 200 mL-glass flask equipped with a condenser and a Dean-Stark apparatus was charged with 20.0 g of α-methoxyisobutyric acid obtained in Reference Example 1, 30.0 g of n-propanol (available from Wako Pure Chemical Industries, Ltd.), 0.96 g of p-toluenesulfonic acid (available from Wako Pure Chemical Industries, Ltd.), and 10.0 g of toluene (available from Wako Pure Chemical Industries, Ltd.). An esterification reaction was performed under heating and reflux at normal pressure. The reaction was performed for 5 hours while water produced was extracted by the Dean-Stark apparatus. After washing with an aqueous sodium hydroxide solution and then with an saturated aqueous solution of sodium chloride, distillation under reduced pressure was performed to obtain 15.9 g of n-propyl α-methoxyisobutyrate (GC purity: 99.9%) as a fraction at 81 hPa and 94° C. The reaction formula for this reaction is shown as Formula (6) below.

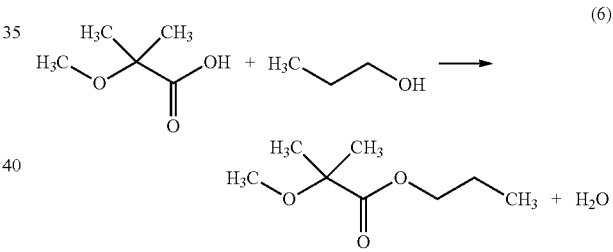

(6)

Examples 2 to 3: Synthesis of Various α-Methoxyisobutyric Esters

Using a reaction apparatus similar to that of Example 1, an appropriate amount of α-methoxyisobutyric acid and each alcohol (isopropanol, cyclopentanol) were subjected to esterification in the presence of an appropriate catalyst such as p-toluenesulfonic acid and in some cases in the co-presence of a solvent such as hexane or toluene, under appropriate reaction conditions with heating. The esterification was completed while water produced was extracted by the Dean-Stark apparatus, and the separation operation was performed in the same manner as in Example 1 to obtain each of α-methoxyisobutyric esters below. The GC purity of the obtained α-methoxyisobutyric esters is also shown.

Isopropyl α-methoxyisobutyrate (GC purity: 99.9%)

Cyclopentyl α-methoxyisobutyrate (GC purity: 98.2%)

The results of aroma evaluation performed by perfumers for the various α-methoxyisobutyric esters obtained by the method described above are shown in Table 1.

TABLE 1

| | Structural formula | Aroma evaluation |
|---|---|---|
| Example 1 | [Structure: H3C-O-C(CH3)2-C(=O)-O-CH2-CH3] | Mint-like aroma having a cool feeling<br>Lime-like citrus aroma<br>Spicy aroma<br>White floral aroma<br>Herbal aroma |
| Example 2 | [Structure: H3C-O-C(CH3)2-C(=O)-O-CH(CH3)-CH3] | Mint-like aroma having a refreshing feeling<br>Lime-like citrus aroma<br>White floral aroma<br>Spicy aroma<br>Woody aroma (damascone-like) |
| Example 3 | [Structure: H3C-O-C(CH3)2-C(=O)-O-cyclopentyl] | Fresh mint-like aroma<br>Lemon-like citrus aroma<br>Floral aroma<br>Spicy aroma<br>Herbal green aroma |

<Evaluation of Biodegradability and Bioconcentration of Fragrance Materials>

One of methods for evaluating biodegradability of a compound is the OECD test guideline 301 C. In accordance with the method, assessment of biodegradability is possible for the compound from the biochemical oxygen demand and the actual rate of oxygen uptake in an aqueous solution in which the compound and aerobic microorganisms coexist.

Calculation software "Biowin5" and "Biowin6" is known and used in a method for easily and accurately estimating the probability of biodegradation of the compound in compliance with this test method.

In addition, one method for evaluating bioconcentration of compounds is the OECD test guideline 305. In accordance with the method, the degree of concentration can be determined from the amount of a compound incorporated into a fish body when the compound is exposed to the fish. Calculation software "BCFWIN" is known as a method for easily and accurately estimating the degree of bioconcentration of the compound in compliance with this test method.

The software is available to the public as one of modules of calculation software called "The Estimations Programs Interface for Windows version 4.1", created by the United States Environmental Protection Agency (EPA) for the purpose of evaluating the environmental effects of chemical substances, and is used in the compound classification for The Globally Harmonized System of Classification and Labelling of Chemicals (GHS) and the review of new chemical substances by the United States Environmental Protection Agency. This software was used to evaluate the difference in biodegradability and bioconcentration between existing fragrance materials and the compounds according to an embodiment of the present invention.

Menthol, menthone, and carvone, having a mint-like tone and (E)-α-damascone and (E)-β-damascenone, having a fruity tone, were selected as representative examples of existing fragrance materials similar to the compounds according to an embodiment of the present invention, and evaluated along with the compounds according to an embodiment of the present invention. The SMILES formulas used for input to the software and the output results of the probabilities of good degradability by "Biowin5 (linear prediction model)" and "Biowin6 (non-linear prediction model)" are shown in Table 2. A larger value of the results indicates better degradability: for a value of 0.5 or greater, the compound was rated as having good degradability (symbol "A" in the table), and for a value of less than 0.5, the compound was rated as having low degradability (symbol "B" in the table).

In addition, as evaluation of the bioconcentration by "BCFWIN version 3.01", the output results according to both the "regression-based method" and "Arnot-Gobas method" are shown in Table 2. In both the methods, a larger value means much concentration from the environment to the fish bodies. Such a value serves as an indicator showing an adverse effect on the environment caused by the food chain.

From Table 2, the results obtained show that the compounds according to an embodiment of the present invention were expected to have good biodegradability and low bioconcentration with respect to menthol, menthone, carvone, (E)-α-damascone, and (E)-β-damascenone, which were the existing fragrance materials similar to the compounds according to an embodiment of the present invention. The results indicated that the compounds according to an embodiment of the present invention are easily biodegraded and unlikely to be bioconcentrated after being released into the environment as fragrances, and thus exhibited a lower impact on the environment.

TABLE 2

| | Structural formula | SMILES | Biodegradability | | | | Bioconcentration (L/kg wet-wt) | |
|---|---|---|---|---|---|---|---|---|
| | | | Biowin5 | | Biowin6 | | BCFWIN | BCFWIN Arnot- |
| | | | Degradation probability | Score | Degradation probability | Score | BCFWIN regression-based method | Gobas method (upper trophic) |
| Example 1 | (structure) | CC(C(OCCC)=O)(C)OC | 0.749 | A | 0.829 | A | 4.28 | 2.33 |
| Example 2 | (structure) | CC(C(OC(C)C)=O)(C)OC | 0.600 | A | 0.654 | A | 3.82 | 2.10 |
| Example 3 | (structure) | CC(C(OC1CCCC1)=O)(C)OC | 0.663 | A | 0.682 | A | 1.43 | 9.27 |
| Comparative Example 1 | (Menthol) | CC(C)C1CCC(C)CC1O | 0.455 | B | 0.331 | B | 59.16 | 23.33 |
| Comparative Example 2 | (Menthone) | CC(C)C1CCC(C)CC1=O | 0.406 | B | 0.335 | B | 47.75 | 74.13 |
| Comparative Example 3 | (Carvone) | C=C(C)C(C1)CC=C(C)C1=O | 0.454 | B | 0.375 | B | 28.51 | 43.35 |
| Comparative Example 4 | ((E)-alpha-damascone) | CC1(C)C(C(/C=C/C)=O)C(C)=CCC1 | 0.398 | B | 0.216 | B | 316.2 | 586.1 |
| Comparative Example 5 | ((E)-beta-damascenone) | CC1(C)C(C(/C=C/C)=O)=C(C)C=CC1 | 0.378 | B | 0.213 | B | 278.0 | 527.2 |

Example 4: Floral-Type Fragrance Composition

A fragrance composition was prepared by adding 19.5 parts by mass of isopropyl α-methoxyisobutyrate obtained in Example 2 to 80.5 parts by mass of a fragrance composition having composition shown in Table 3.

According to the aroma evaluation by perfumers, addition of the isopropyl α-methoxyisobutyrate of Example 2 to the fragrance composition having the composition described in Table 3 softened the green nuance, improved the integrity, and enhanced the intensity and volume of the scent. As a result, provided was a floral-type fragrance composition to which a clean and calm floral aroma was imparted and lime-like citrusness, floralness, spiciness, woodiness, and a mint-like refreshing feeling were imparted. The aroma of this fragrance composition seems to be suitable for perfuming men's hair mousse, men's facial foam, men's skin cream, and the like.

TABLE 3

| Blend ingredients | parts by mass |
|---|---|
| Bergamot oil (10%) | 13.1 |
| Phenethyl alcohol | 9.6 |
| α-Ionone | 8.6 |
| Hexyl salicylate | 8.6 |

TABLE 3-continued

| Blend ingredients | parts by mass |
|---|---|
| Ylang ylang oil (10%) | 8.0 |
| Benzyl acetate | 7.4 |
| Hydroxycitronellal | 6.2 |
| α-Hexyl cinnamaldehyde | 5.3 |
| Styralyl acetate | 4.8 |
| cis-Jasmone | 4.6 |
| B-Ionone | 2.2 |
| γ-Undecalactone | 2.1 |
| Total | 80.5 |

*Blend ingredients in parentheses in the table were used as a solution diluted with dipropylene glycol. The figures represent mass % of the fragrance included in the solution.

INDUSTRIAL APPLICABILITY

An α-methoxyisobutyric ester compound according to an embodiment of the present invention has an excellent aroma and is expected to be used itself as a fragrance. Additionally, use of the compound as a fragrance ingredient can provide a fragrance composition excellent in aroma properties. The composition, when blended in a variety of products, exhibits desired perfuming properties.

Furthermore, it was shown that the compounds obtained in Examples each have excellent biodegradability, low bioconcentration, and a low impact on the environment and are suitable for use.

The invention claimed is:

1. A fragrance composition comprising a compound represented by Formula (1) as an active ingredient:

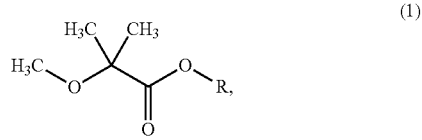

wherein R represents a linear or branched alkyl group having 3 carbon atoms or a cyclic alkyl group having from 3 to 6 carbon atoms.

2. The fragrance composition according to claim 1, wherein R is selected from the group consisting of a n-propyl group, an isopropyl group, and a cyclopentyl group.

3. The fragrance composition according to claim 1, wherein the compound represented by the formula (1) imparts a mint-like scent.

4. The fragrance composition according to claim 1, wherein in the compound of the formula (1) in which R is an isopropyl group imparts a damascone-like fruity-tone, floral-tone, or woody-tone scent.

* * * * *